United States Patent [19]
Laas et al.

[11] Patent Number: 5,750,629
[45] Date of Patent: May 12, 1998

[54] URETDIONE DIISOCYANATES AND A PROCESS FOR THEIR PRODUCTION

[75] Inventors: Hans-Josef Laas, Köln; Reinhard Halpaap, Odenthal; Josef Pedain, Köln; Klaus König, Odenthal, all of Germany

[73] Assignee: Bayer Aktiengesellschaft, Leverkusen, Germany

[21] Appl. No.: 788,726

[22] Filed: Jan. 23, 1997

[30] Foreign Application Priority Data

Jan. 30, 1996 [DE] Germany ................. 196 03 245.8

[51] Int. Cl.$^6$ ............... C08G 18/79; C08G 18/80; C07D 229/00
[52] U.S. Cl. ................. 528/45; 252/182.2; 252/182.21; 528/67; 528/73; 540/202; 548/951; 548/952; 560/336; 560/352
[58] Field of Search ............... 540/202; 252/182.2, 252/182.21; 528/45, 67, 73; 560/336, 352; 548/951, 952

[56] References Cited

U.S. PATENT DOCUMENTS

| | | | |
|---|---|---|---|
| 4,463,154 | 7/1984 | Disteldorf et al. | 528/45 |
| 4,476,054 | 10/1984 | Disteldorf et al. | 540/202 |
| 4,595,534 | 6/1986 | Scholl | 540/202 |
| 4,614,785 | 9/1986 | Richter et al. | 528/45 |
| 4,668,780 | 5/1987 | Disteldorf et al. | 540/202 |
| 4,912,210 | 3/1990 | Distelford et al. | 540/202 |
| 4,929,724 | 5/1990 | Engbert et al. | 540/202 |
| 5,043,092 | 8/1991 | Pedain et al. | 252/181.21 |
| 5,143,994 | 9/1992 | Laas et al. | 528/73 |
| 5,149,766 | 9/1992 | Bruchmann | 528/49 |
| 5,216,107 | 6/1993 | Pedain et al. | 540/202 |
| 5,237,058 | 8/1993 | Laas et al. | 540/202 |
| 5,596,066 | 1/1997 | Laas et al. | 528/75 |
| 5,621,064 | 4/1997 | Laas et al. | 528/60 |

FOREIGN PATENT DOCUMENTS 1258009 8/1989 Canada.

OTHER PUBLICATIONS

J. Prakt. Chem. 336 1994, 185–200.

P. Müller et al. Anew. Makromol. Chem. 65 1977, 23–39.

F. Schmitt, XIXth Fatipac Kongress, vol. III, Aachen 1988, pp. 211ff.

Primary Examiner—Rabon Sergent
Attorney, Agent, or Firm—Joseph C. Gil; Thomas W. Roy

[57] ABSTRACT

The present invention relates to a process for preparing pure bis(isocyanatoalkyl)monouretdiones corresponding to formula (I)

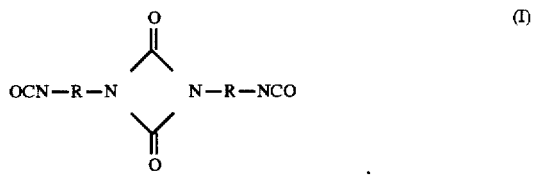

wherein R represents identical or different, linear or branched alkyl groups having 4 to 9 carbon atoms.

by oligomerizing at least a portion of the isocyanate groups of aliphatic diisocyanates in the presence of catalysts which accelerate the dimerization of isocyanate groups, terminating the reaction at the desired degree of oligomerization, removing unreacted excess diisocyanate by extraction or thin film distillation to obtain a distillation residue, subjecting the distillation residue to thin film distillation at a temperature of 160° to 220° C. and a pressure of 0.01 to 1.0 mbar and obtaining bis(isocyanato-alkyl)monouretdiones corresponding to formula (I) as the distillate. The present invention also relates to the resulting bis(isocyanato-alkyl) monouretdiones corresponding to formula I and to their use for the production of polyisocyanate addition products, in particular as the isocyanate components in polyurethane coatings compositions, in which the isocyanate groups may optionally be present in blocked form.

20 Claims, No Drawings

URETDIONE DIISOCYANATES AND A PROCESS FOR THEIR PRODUCTION

BACKGROUND OF THE INVENTION

1. Field of the Invention

The present invention relates to pure bis(isocyanato-alkyl)-monouretdiones, to a method for their preparation, to their use as starting components for preparing polyurethane plastics, in particular as the isocyanate component in polyurethane coating compositions, and to the resulting coating compositions.

2. Description of the Prior Art

The preparation of oligomeric aliphatic polyisocyanates containing uretdione structures by the catalytic oligomerization of a portion of the isocyanate groups of monomeric aliphatic diisocyanates, termination of the reaction at the desired degree of conversion and removal of excess unreacted diisocyanate by film distillation is known. A comprehensive survey of the industrially relevant dimerization methods of the prior art may be found in J. Prakt. Chem. 336 (1994) 185–200.

Because the starting compounds are difunctional, in all of the known methods for preparing polyisocyanates containing uretdione structures the reaction products are not obtained in the form of pure compounds, but invariably as mixtures of oligomers having a various molecular weights. The products may also contain compounds containing isocyanurate groups (trimers) in addition to compounds containing uretdione groups. The composition of the product is directly dependent on the degree of modification of the starting monomers such that the properties of the products, such as average molecular weight, average isocyanate functionality and viscosity, can be selected within certain ranges. A greater degree of conversion (i.e., terminating the reaction at a lower NCO content) results in an increase in the average molecular weight and an increase in viscosity, while a lower degree of conversion results in larger quantities of low molecular weight oligomers.

Pure monouretdione diisocyanates, i.e., those formed from exactly two molecules of starting diisocyanate, cannot be prepared by known methods. But such "dimeric diisocyanates," which are free from higher molecular weight components, are of great interest, for example, as cross-linking agents for two-component polyurethane coatings having a low solvent content because of their particularly low viscosity.

Accordingly, it is an object of the present invention to provide a method for preparing bis(isocyanatoalkyl) monouretdiones in pure form.

This object may be achieved in accordance with the present invention. The invention is based on the observation that aliphatic monouretdione diisocyanates formed from exactly two molecules of diisocyanate can be separated from known mixtures of oligomers having a low monomer content by vacuum distillation in suitable, commercially available film evaporators at temperatures of above 160° C., without decomposing the uretdione structures into monomeric isocyanates to a great extent.

The ability to obtain such products according to the present invention is surprising because the catalytic dimerization of isocyanates is generally known to be reversible by heat, which is why uretdiones are regarded as "internally blocked" isocyanate groups. In the literature generally a temperature of about 160° C. is disclosed as the deblocking temperature, i.e., decomposition temperature, of uretdione groups (for example, P. Müller et al, Angew. Makromol. Chem. 65 (1977), 23; F. Schmitt, XIXth Fatipec Kongress, Vol. III, Aachen 1988, pages 211 ff.). Above this temperature a considerable degree of uretdione decomposition is expected. For this reason the mildest distillation conditions are used for separating unreacted starting monomers during the preparation of oligomeric polyisocyanates containing uretdione groups (cf. for example, EPA 178 520 and EPA 337 116).

SUMMARY OF THE INVENTION

The present invention relates to a process for preparing pure bis(isocyanatoalkyl)-monouretdiones corresponding to formula (I)

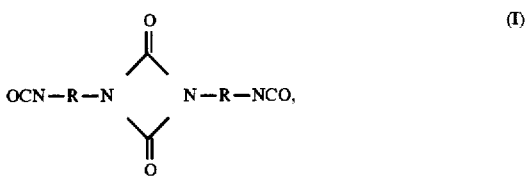

wherein R represents identical or different, linear or branched alkyl groups having 4 to 9 carbon atoms, by oligomerizing a portion of the isocyanate groups of diisocyanates corresponding to formula (II)

in the presence of catalysts or which accelerate the dimerization of isocyanate groups, terminating the reaction at the desired degree of oligomerization, removing unreacted excess diisocyanate by extraction or thin film distillation to obtain a distillation residue, subjecting the distillation residue to thin film distillation at a temperature of 160° to 220° C. and a pressure of 0.01 to 1.0 mbar and obtaining bis(isocyanato-alkyl)monouretdiones corresponding to formula (1) as the distillate.

The present invention also relates to the resulting bis (isocyanato-alkyl)monouretdiones corresponding to formula 1.

Finally, the present invention relates to the use of these bis(isocyanatoalkyl)monouretdiones for the production of polyisocyanate addition products, in particular as the isocyanate components in polyurethane coatings compositions, in which the isocyanate groups may optionally be present in blocked form.

DETAILED DESCRIPTION OF THE INVENTION

Starting materials for the method according to the invention are selected from aliphatic diisocyanates corresponding to formula (II) and mixtures of these diisocyanates such as 1,4-diisocyanatobutane, 1,6-diisocyanatohexane (hexamethylene diisocyanate, HDI), 1,5-diisocyanato-2,2-dimethylpentane and 2,2,4- or 2,4,4-trimethyl-1,6-diisocyanatohexane. Preferred diisocyanates are those corresponding to formula (II) wherein the R represents a linear or branched alkyl group having 4 to 6 carbon atoms. HDI is particularly preferred.

Suitable catalysts for use in the process according to the invention are all known compounds which catalyze the dimerization of aliphatic isocyanate groups. Examples include tertiary organic phosphines (for example, U.S. Pat. No. 4,614,785, column 4, lines 11 to 47; DE-A 1,934,763 and DE-A 3,900,053); peralkylated aminophosphines (for example, DE-A 3,030,513, DE-A 3,227,779 and DE-A 3,437,635); 4-dialkylaminosubstituted pyridines (DE-A 3,739,549); antimony pentafluoride (DE-A 3,420,114) and boron trifluoride (DE-A 1,670,720).

Compounds containing trivalent phosphorus, such as tertiary organic phosphines or peralkylated aminophosphines, are preferably used as catalysts in the process according to the invention. Particularly preferred catalysts are tributylphosphine and trioctylphosphine.

The catalysts employed in the process according to the invention are preferably added in quantities of 0.01 to 5 wt. %, more preferably 0.1 to 2 wt. %, based the weight of the starting diisocyanate.

Suitable cocatalysts may optionally be used in the process according to the invention in addition to the above-mentioned catalysts. These cocatalysts include organic compounds having at least one hydrogen atom bound to oxygen, nitrogen or sulphur, and a $pK_a$ of at least 6, such as those described in DE-A 3,437,635, page 11, line 8 to page 16, line 6 (U.S. Pat. No. 4,929,724, herein incorporated by reference).

Preferred cocatalysts are low molecular weight, monohydric or polyhydric alcohols having a molecular weight of 32 to 200, or mixtures of these alcohols. Examples include methanol, ethanol, n-propaiol, isopropanol, n-butanol, n-hexanol, 2-ethyl-1-hexanol, 1-methoxy-2-propanol, ethylene glycol, propylene glycol, the isomeric butanediols, hexanediols and octanediols, diethylene glycol, dipropylene glycol, 2-ethyl-1,3-hexanediol, 2,2,4-trimethylpentanediol, glycerol, trimethylol-propane and mixtures of these and/or other alcohols.

The cocatalysts are used in the process according to the invention, if at all, in quantities of up to 5 wt. %, preferably of 0.5 to 3 wt. %, based on the weight of the starting diisocyanate.

The actual cocatalysts are the reaction products of the starting diisocyanate with the optional cocatalysts used in the process according to the invention. Therefore, instead of using the previously mentioned isocyanate-reactive compounds as co-catalysts, it is also possible to use separately obtained reaction products of these compounds with starting diisocyanate, for example, urethanes obtained by reacting the preferred alcoholic cocatalysts with diisocyanate.

Suitable catalyst poisons for terminating the oligomerization reaction include alkylating agents such as dimethyl sulphate or methyl p-toluenesulphonate; acylating agents such as benzoyl chloride; acids such as perfluorobutanesulphonic acid; sulphur; or sulphonyl isocyanates, which are given as examples in U.S. Pat. No. 4,614,785, column 5, line 27 to column 6, line 35. Silylated acids (EP-A 520,210) and oxidizing agents such as organic (hydro)peroxides, peroxycarboxylic acids or oxygen (EP-A 481,318) are also suitable for use as catalyst poisons.

The quantity of catalyst poison necessary to terminate the reaction depends on the quantity of catalyst used; an equimolar quantity of the catalyst poison, based on the weight of the dimerization catalyst, is preferably used. However, if allowance is made for losses of catalyst that may occur during the reaction, then 20 to 80 equivalent-% of the catalyst poison, based on the weight of catalyst originally used, may be sufficient to stop the reaction.

If substituted pyridine catalysts are used, it is possible to dispense entirely with the use of a catalyst poison. When the desired degree of oligomerization has been reached, the catalyst, without prior deactivation, is then separated from the reaction product by distillation together with the unreacted starting diisocyanate.

The process according to the invention is preferably carried out in the melt, but may also be carried out in the presence of solvents which are inert to isocyanate groups. Suitable solvents include hexane, toluene, xylene, chlorobenzene, ethyl acetate, ethyl butyrate, ethylene glycol acetate, propylene glycol monomethyl ether acetate, acetone, methyl isobutyl ketone, methylene chloride, N-methylpyrrolidone or mixtures of these and/or other solvents.

The oligomerization reaction according to the invention is carried out in a known manner, as described, for example, in DE-A 1,670,720, 1,954,093, 3,437,635 (U.S. Pat. No. 4,929, 724, herein incorporated by reference) or 3,739,549 (U.S. Pat. No. 4,912,210, herein incorporated by reference). In general the procedure is to heat the starting diisocyanate, optionally under an inert gas, such as nitrogen, and optionally in the presence of a suitable solvent, to a temperature of 20° to 100° C., preferably 40° to 70° C. The optional cocatalyst may then be added. Thereafter, optionally after the end of the reaction which takes place spontaneously between cocatalyst and starting diisocyanate, a dimerization catalyst is added in the quantity set forth and the reaction temperature is adjusted by suitable means (heating or cooling) to a temperature of 40° to 120° C., preferably 50° to 80° C. In general the reaction is terminated when a degree of oligomerization of 10 to 60%, preferably 10 to 40%, has been reached.

"Degree of oligomerization" means the percentage of isocyanate groups present in the initial mixture which are consumed during the reaction by dimerization, trimerization and, when cocatalysts are used, by reaction with isocyanate groups (for example, urethanization). The degree of oligomerization is generally obtained after a reaction time of 1 to 48 hours, preferably 2 to 24 hours. The reaction can be terminated by adding a catalyst poison and then optionally briefly heating of the reaction mixture to a temperature above 80° C., preferably above 120° C.

The reaction mixture is then generally freed from volatile constituents (excess monomeric diisocyanates, optional solvents and catalyst when a catalyst poison is not used) by distillation under high vacuum, preferably in a film evaporator, under conditions as mild as possible, for example, at a temperature of 100° to 160° C., preferably 120° to 140° C.

In a less preferred embodiment of the process according to the invention, the volatile constituents are separated from the oligomerization product by extraction with solvents that are inert to isocyanate groups, for example, aliphatic or cycloaliphatic hydrocarbons such as pentane, hexane, heptane, cyclopentane or cyclohexane.

After separation of volatile constituents, mixtures of polyisocyanates are obtained which are virtually colorless, are liquid at room temperature, possess uretdione groups and optionally isocyanurate groups and generally contain less than 5 wt. %, less than 2 wt. % and more preferably less than 1 wt. % of monomeric starting diisocyanates.

The mixtures of polyisocyanates are then subjected to a further distillation step in order to separate the pure bis (isocyanatoalkyl)uretdiones in known film evaporators, especially short-path evaporators, such as those employed for the above-mentioned separation of the monomeric starting diisocyanates. The distillation is carried out at a temperature above 160° C., preferably 165° to 220° C. and more preferably 170° to 200° C., under high vacuum, for example, at a pressure of less than 1.0 mbar, preferably less than 0.5 mbar and more preferably less than 0.2 mbar.

The resulting distillates predominantly contain the desired pure bis(isocyanatoalkyl)monouretdiones in addition to smaller amounts of monomeric starting diisocyanates. These monomers are made up of the monomeric polyisocyanates used as raw materials and, to a small extent monomers reformed during the distillation due to the thermal decomposition of uretdione groups. The monomers may, if necessary, be removed by an additional distillation under mild conditions or by extraction, as previously described for the separation of volatile constituents from the reaction mixture following oligomerization.

The various distillation steps of the process according to the invention may advantageously be carried out in a special distillation apparatus containing three evaporation stages connected to one another. In the first stage, the reaction mixture obtained by oligomerization is freed from volatile constituents, in particular from the monomeric starting diisocyanates, under the conditions described above at temperatures as low as possible. The mixture of oligomeric polyisocyanates obtained as the distillation residue is then introduced without further separation into a second evaporator unit, preferably a short-path evaporator. Here the actual separation, essential to the invention, of the pure monouretdione diisocyanates from the mixture of oligomers then takes place at a temperature above 160° C. The monouretdione diisocyanates, which are obtained as distillate in this second distillation stage, pass through the third distillation step wherein, again under conditions as mild as possible, residual monomers which may still be present are removed.

The pure bis(isocyanatoalkyl)monouretdiones obtained according to the invention are present in the form of clear, colorless liquids, which are shown from analysis by gel permeation chromatography (GPC) to contain at least 97 wt. %, preferably 98 to 99.9 wt. %, of dimers of the starting diisocyanates; less than 2 wt. %, preferably less than 1.5 wt. % and more preferably less than 1.0 wt. % of higher molecular weight oligomers; and less than 0.5 wt. %, preferably less than 0.2 wt. % and more preferably less than 0.1 wt. % of residual monomers. The monouretdiones have a titrimetrically determined content of free isocyanate groups of 20.0 to 30.1 wt. %, preferably 24.9 to 30.1 wt. % and more preferably 24.9 to 25.1 wt. %.

These pure monouretdione diisocyanates are superior to the known oligomeric uretdione polyisocyanates of the prior art, in particular, due to their very low viscosities, which are generally less than 250 mPa.s at 23° C., in accordance with DIN 53 018. For example, the bis(6-isocyanatohexyl)-monouretdione obtained from HDI as the starting diisocyanate has a viscosity of only 30 mPa.s (at 23° C.).

The mixtures of oligomers containing uretdione groups and optionally isocyanurate groups, which remain as distillation residue after the removal of the bis(isocyanatoalkyl) monouretdiones by distillation according to the invention, are virtually colorless resins having viscosities that are only slightly higher than those of the mixtures of polyisocyanates obtained by the known prior art dimerization methods. They generally contain less than 0.5 wt. %, preferably less than 0.3 wt. % and more preferably less than 0.2 wt. % of monomeric starting diisocyanates and possess isocyanate group contents of 14.5 to 24.5 wt. %, preferably 19.0 to 24.5 wt. % and more preferably 19.0 to 20.5 wt. %.

Both the bis(isocyanatoalkyl)monouretdiones obtainable by the process according to the invention and the "dimer-poor" mixtures of polyisocyanates containing uretdione groups and optionally isocyanurate groups are valuable starting materials for the production of polyisocyanate polyaddition products, preferably polyurethane plastics, by reaction with compounds containing isocyanate-reactive groups. They are especially useful in one-component or two-component polyurethane coating compositions. In blocked form using known blocking agents for isocyanate groups, they are also valuable starting materials for one-component polyurethane stoving varnishes.

Due to their exceptionally low viscosity, the pure bis(isocyanato-alkyl)uretdiones are of great interest, particularly as cross-linking components for two-component polyurethane coating composition, which have a low solvent content. The bis(isocyanatoalkyl)monouretdiones may also be preferably used as crosslinking agents for polyurethane powder coatings curable by heat (for example, as described in EP-A 45,994, EP-A 45,996, EPA 45,998 and EP-A 639,598).

In the following examples all parts and percentages are by weight, unless otherwise indicated.

EXAMPLES

Example 1

100 g (1.1 moles) of 1,3-butanediol and 30 g (0.15 moles) of tri-n-butylphosphine were stirred successively at room temperature into 10 kg (59.5 moles) of hexamethylene diisocyanate (HDI) and the mixture was then heated to 60° C. After a reaction time of 4.5 hours, the NCO content of the reaction mixture was 42.5%, corresponding to a degree of oligomerization of 15%. The reaction was stopped by adding 28 g (0.15 moles) of methyl toluenesulphonate and heating at 80° C. for one hour. After this unreacted excess HDI was removed by distillation in a film evaporator at a temperature of 130° C. and a pressure of 0.5 mbar.

The resulting mixture of oligomers low in monomers had an NCO content of 21.6%, a viscosity (in accordance with DIN 53 018) of 240 inPa.s (23° C.), a HAZEN color index of about 50 and the following composition from analysis by gel permeation chromatography (GPC):

monomeric HDI: 0.3%

HDI uretdione (n=2): 39.0%

HDI isocyanurate (n=3): 22.6% higher oligomers: 38.1%

1000 g of this mixture of oligomers was distilled in a commercially available shortpath evaporator at a temperature of 180° C. and a pressure of 0.1 mbar in order to separate the pure monouretdione diisocyanate.

670 g of a liquid polyisocyanate having an NCO content of 19.5%, a viscosity of 690 mPa.s (23° C.) and a HAZEN color index of 65 were obtained as the distillation residue. When analyzed by GPC, the residue had the following composition:

monomeric HDI: not detectable

HDI uretdione (n=2): 19.4%

HDI isocyanurate (n=3): 28.7% higher oligomers: 51.9%

The colorless distillate obtained was subjected to a further thin film distillation at a temperature of 130° C. and a pressure of 0.2 mbar in order to remove the monomeric HDI. 275 g of virtually pure bis(6-isocyanato-hexyl)uretdione having an NCO content of 25.0%, a viscosity of 30 mPa.s (23° C.) and a HAZEN color index of about 10 were obtained as the distillation residue from the third distillation stage. This corresponded to a yield of 27.5%, based on the weight of the mixture of oligomers obtained as the residue from the first distillation stage. When analyzed by GPC the product obtained by the process according to the invention had the following composition:

monomeric HDI: not detectable
HDI uretdione (n=2): 99.1%
HDI isocyanurate (n=3): 0.3%
higher oligomers: 0.6%

Example 2

1000 g of the mixture of oligomers low in monomers described in Example 1 were distilled in a commercially available short-path evaporator (second distillation stage) at a temperature of 190° C. and a pressure of 0.1 mbar.

710 g of a liquid polyisocyanate having an NCO content 19.9%, a viscosity of 660 mPa.s (23° C.) and a HAZEN color index of 70 were obtained as the distillation residue. When analyzed by GPC, the residue had the following composition:

monomeric HDI: 0.3%
HDI uretdione (n=2): 20.8%
HDI isocyanurate (n=3): 27.6%
higher oligomers: 51.3%

The colorless distillate obtained was subjected to a fuirther thin film distillation at a temperature of 130° C. and a pressure of 0.1 mbar in order to remove the monomeric HDI.

223 g of virtually pure bis(6-isocyanatohexyl)uretdione having an NCO content of 25.0%, a viscosity of 32 mPa.s (23° C.) and a HAZEN color index of 10 were obtained as the distillation residue from the third distillation stage. This corresponded to a yield of 22.3%, based on the weight of the mixture of oligomers obtained as the residue from the first distillation stage. When analyzed by GPC the product obtained by the process according to the invention had the following composition:

monomeric HDI: not detectable
HDI uretdione (n=2): 98.5%
HDI isocyanurate (n=3): 0.5%
higher oligomers: 1.0%

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing bis(isocyanatoalkyl)-monouretdiones corresponding to formula (I)

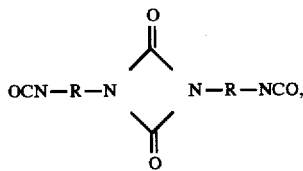

wherein R represents identical or different, linear or branched alkyl groups having 4 to 9 carbon atoms, which comprises oligomerizing at least a portion of the isocyanate groups of a diisocyanate corresponding to formula (II)

OCN—R—NCO,   (II)

in the presence of a catalyst which accelerates the dimerization of isocyanate groups, terminating the reaction at the desired degree of oligomerization, removing unreacted excess diisocyanate by extraction or thin film distillation to obtain a distillation residue, subjecting the distillation residue to thin film distillation at a temperature of 160° to 220° C. and a pressure of 0.01 to 1.0 mbar and obtaining bis(isocyanatoalll)-monouretdiones corresponding to formula (1) as the distillate.

2. The process of claim 1 wherein said alkyl groups are linear alkyl groups having 4 to 6 carbon atoms.

3. The process of claim 1 wherein said alkyl groups are linear alkyl groups having 6 carbon atoms.

4. The process of claim 1 wherein said catalyst comprises a trivalent phosphorus compound.

5. The process of claim 2 wherein said catalyst comprises a trivalent phosphorus compound.

6. The process of claim 3 wherein said catalyst comprises a trivalent phosphorus compound.

7. The process of claim 1 wherein said catalyst comprises tributylphosphine or trioctylphosphine.

8. The process of claim 2 wherein said catalyst comprises tributylphosphine or trioctylphosphine.

9. The process of claim 3 wherein said catalyst comprises tributylphosphine or trioctylphosphine.

10. The process of claim 1 wherein the distillate contains at least 97 wt. % of bis(isocyanatoalkyl)-monouretdiones.

11. The process of claim 2 wherein the distillate contains at least 97 wt. % of bis(isocyanatoalkyl)-monouretdiones.

12. The process of claim 3 wherein the distillate contains at least 97 wt. % of bis(isocyanatoalkyl)-monouretdiones.

13. The process of claim 4 wherein the distillate contains at least 97 wt. % of bis(isocyanatoalkyl)-monouretdiones.

14. The process of claim 6 wherein the distillate contains at least 97 wt. % of bis(isocyanatoalkyl)-monouretdiones.

15. The process of claim 9 wherein the distillate contains at least 97 wt. % of bis(isocyanatoalkyl)-monouretdiones.

16. A polyisocyanate mixture containing at least 97 wt. % of bis(isocyanatoalkyl)-monouretdiones corresponding to formula (I)

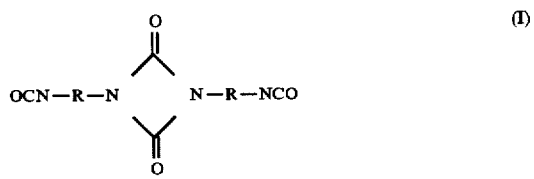

wherein R represents identical or different, linear or branched alkyl groups having 4 to 9 carbon atoms.

17. The polyisocyanate mixture of claim 16 wherein said alkyl groups are linear alkyl groups having 4 to 6 carbon atoms.

18. The polyisocyanate mixture of claim 16 wherein said alkyl groups are linear alkyl groups having 6 carbon atoms.

19. A composition containing the polyisocyanate mixture of claim 16 and a compound containing isocyanate-reactive groups.

20. A coating composition comprising a compound containing isocyanate-reactive groups and the polyisocyanate mixture of claim 16, wherein the free isocyanate groups of formula (I) are optionally blocked with a blocking agent for isocyanate groups.

* * * * *